United States Patent [19]
Coulie et al.

[11] Patent Number: 5,830,753
[45] Date of Patent: Nov. 3, 1998

[54] ISOLATED NUCLEIC ACID MOLECULES CODING FOR TUMOR REJECTION ANTIGEN PRECURSOR DAGE AND USES THEREOF.

[75] Inventors: Pierre Coulie; Hideyuki Ikeda; Thierry Boon-Falleur, all of Brussels, Belgium

[73] Assignee: Ludwig Institute for Cancer Research, New York, N.Y.

[21] Appl. No.: 316,231

[22] Filed: Sep. 30, 1994

[51] Int. Cl.$^6$ .............................. C12N 5/00; C07H 21/04; C07K 14/00
[52] U.S. Cl. ...................... 435/325; 435/69.1; 435/325; 435/320.1; 435/252.3; 536/23.5; 530/350
[58] Field of Search .......................... 536/23.5; 435/69.1, 435/325, 320.1, 252.3; 935/9, 70, 71; 530/350

[56] References Cited

U.S. PATENT DOCUMENTS 5,342,774  8/1994  Boon et al. .............................. 435/326

FOREIGN PATENT DOCUMENTS

WO9220356  11/1992  WIPO .
WO9403205  2/1994  WIPO .

OTHER PUBLICATIONS

Coulie et al, "A New Gene Coding For A Differentiation Antigen Recognized By Autologous Cytolytic T Lymphocytes", J. Exp. Med. 180: 35–42 (Jul. 1994).
Engelhardt, "Structure of Peptides Associated With Class I And Class II Molecules", Ann. Rev. Immunol 12: 181–207 (1994).
Falk et al, "Allele specific peptide ligand motifs of HLA–C– molecules", Proc. Natl. Acad. Sci. USA 90: 12005–12009 (Dec. 1993).
Zemmour et al, "HLA Class I nucleotide sequences, 1992", –Immunogenetics 37: 239–259 (1993).
Rupert et al, "Prominent Role of Secondary Anchor Residues In–Peptide Binding to HLA–A2.1 Molecules", Cell 74: 929–937 (Sep. 10, 1993).
Traversari et al, "A Nonapeptide Encoded by Human Gene MAGE–1 Is–Recognized on HLA–A1 By Cytolytic T Lymphocytes, Directed Against Tumor Antigrn MZ2–E", J. Exp. Med. 176: 1453–1457 (Nov. 1992).
Van der Bruggen et al, "A Gene Encoding An Antigen Recognized–By Cytolytic T Lymphocytes on a Human Melanoma", Science 254: 1643–1647 (1991).
Rötzschke, et al "Isolated and analysis of naturally processed–viral peptides as recognized by cytolytic T cells", Nature 348: 252–254 (Nov. 15, 199).
Bjorkman et al, "The foreign antigen binding site and T cell–recognition of Class I histocompatibility antigens", Nature 329: 512–518 (Oct. 8, 1987).
Robbins, P.F. et al. 1994. Cancer Research, 54: 3124–3126.

*Primary Examiner*—Lila Feisee
*Assistant Examiner*—Minh-Tam Davis
*Attorney, Agent, or Firm*—Felfe & Lynch

[57] ABSTRACT

A new family of tumor rejection antigen precursors, and the nucleic acid molecules which code for them, are disclosed. These tumor rejection antigen precursors are referred to as DAGE tumor rejection antigen precursors, and the nucleic acid molecules which code for them are referred to as GAGE coding molecules. Various diagnostic and therapeutic uses of the coding sequences and the tumor rejection antigens, and their precursor molecules are described.

14 Claims, 2 Drawing Sheets

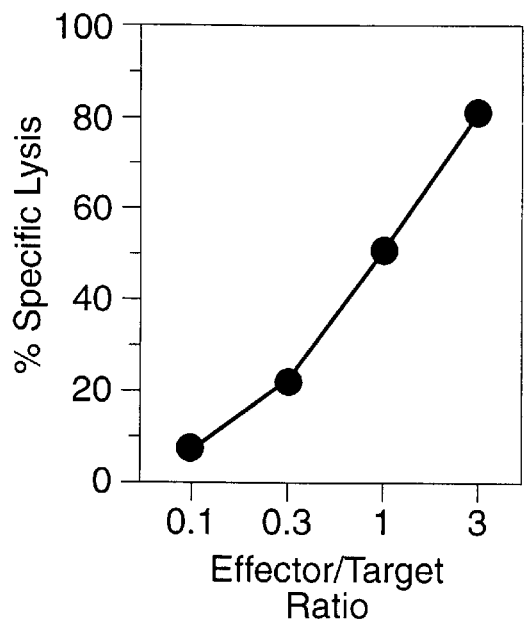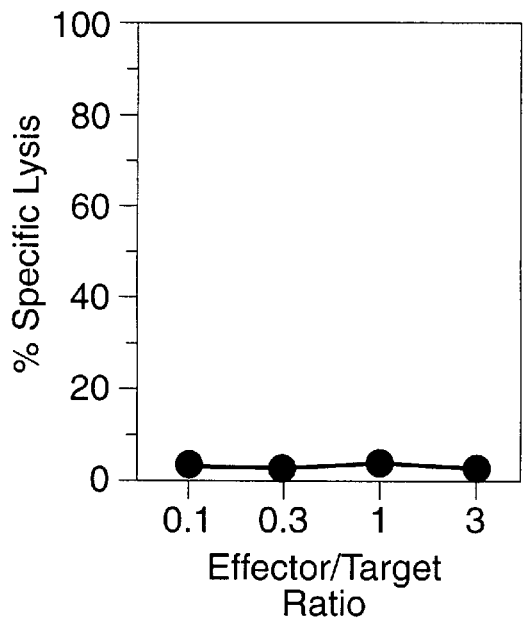
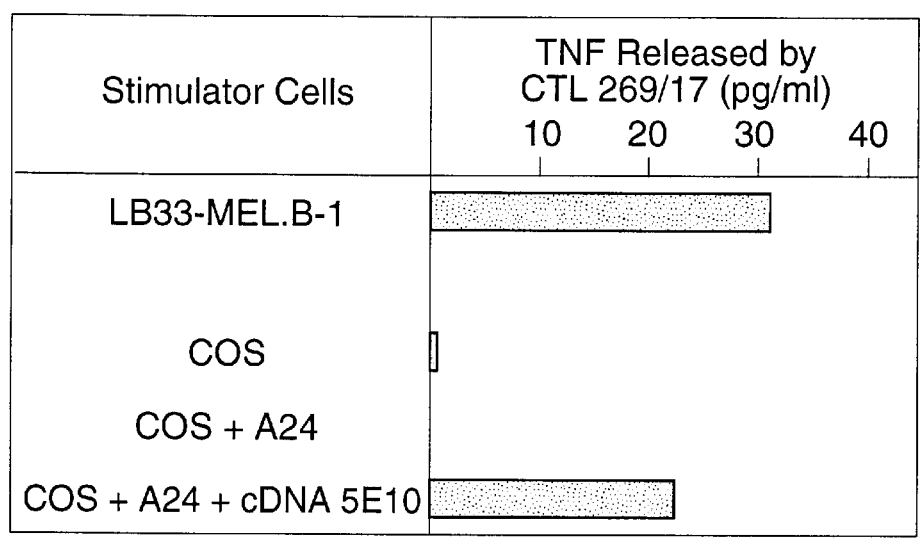

ISOLATED NUCLEIC ACID MOLECULES CODING FOR TUMOR REJECTION ANTIGEN PRECURSOR DAGE AND USES THEREOF.

FIELD OF THE INVENTION

This invention relates to nucleic acid molecules which code for a tumor rejection antigen precursor. More particularly, the invention concerns genes, whose tumor rejection antigen precursor is processed, inter alia, into at least one tumor rejection antigen that is presented by HLA-A24 molecules. The tumor rejection antigen precursor, or "TRAP", may be processed into additional peptides presented by other MHC molecules, such as HLA-A1 and its alleles, HLA-A2, HLA-Cw*1601, HLA-B44, and so forth. The genes in question do not appear to be related to other known tumor rejection antigen precursor coding sequences, are expressed on a variety of tumors and, with the exception of testis cells, are not expressed by normal cells.

BACKGROUND AND PRIOR ART

The process by which the mammalian immune system recognizes and reacts to foreign or alien materials is a complex one. An important facet of the system is the T lymphocyte, or "T cell" response. This response requires that T cells recognize and interact with complexes of cell surface molecules, referred to as human leukocyte antigens ("HLAs"), or major histocompatibility complexes ("MHCs"), and peptides. The peptides are derived from larger molecules which are processed by the cells which also present the HLA/MHC molecule. See in this regard Male et al., Advanced Immunology (J.P. Lipincott Company, 1987), especially chapters 6–10. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides, which, in turn, are expressed on cell surfaces, which can lead to lysis of the tumor cells by specific cytolytic T lymphocytes, or "CTLs" hereafter. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. patent application Ser. No. 807,043, filed Dec. 12, 1991, now U.S. Pat. No. 5,342,774, incorporated by reference in its entirety. The "MAGE" family of tumor rejection antigen precursors is disclosed in this patent.

In U.S. patent application Ser. No. 938,334 now U.S. Pat. No. 5,405,940, the disclosure of which is incorporated by reference, it is explained that the MAGE-1 gene codes for a tumor rejection antigen precursor which is processed to nonapeptides which are presented by the HLA-A1 molecule. The nonapeptides which bind to HLA-A1 follow a "rule" for binding in that a structural motif is satisfied. In this regard, see e.g. PCT/US93/07421; Falk et al., Nature 351: 290–296 (1991); Engelhard, Ann Rev. Immunol. 12: 181–207 (1994); Ruppert et al., Cell 74: 929–937 (1993); Rötzschke et al., Nature 348: 252–254 (1990); Bjorkman et al., Nature 329: 512–518 (1987); Traversari et al., J. Exp. Med. 176: 1453–1457 (1992). The references teach that given the known specificity of particular peptides for particular HLA molecules, one should expect a particular peptide to bind to one HLA molecule, but not to others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 and incorporated by reference, the fact that the MAGE-1 expression product is processed to a second TRA is disclosed. This second TRA is presented by HLA-Cw*1601 molecules. The disclosure shows that a given TRAP can yield a plurality of TRAs, each of which will satisfy a particular motif rule for binding to an MHC molecule.

U.S. patent application Ser. No. 994,928, filed Dec. 22, 1992, and incorporated by reference herein teaches that tyrosinase, a molecule which is produced by some normal cells (e.g., melanocytes), is processed in tumor cells to yield peptides presented by HLA-A2 molecules.

In U.S. patent application Ser. No. 08/032,978, filed Mar. 18, 1993, now U.S. Pat. No. 5,620,886 and incorporated by reference in its entirety, a second TRA, not derived from tyrosinase, is taught to be presented by HLA-A2 molecules. The TRA is derived from a TRAP, but is coded for by a non-MAGE gene. This disclosure shows that a particular HLA molecule may present TRAs derived from different sources.

In U.S. patent application Ser. No.08/079,110, filed Jun. 17, 1993, now U.S. Pat. No. 5,571,711 and incorporated by reference herein, an unrelated tumor rejection antigen precursor, the so-called "BAGE" precursor is described. The BAGE precursor is not related to the MAGE family.

In U.S. patent applications Ser. No. 08/096,039 and Ser. No. 08/250,162, both of which are incorporated by reference, TRAP precursor GAGE, also not related to MAGE, or to BAGE is disclosed.

The work which is presented by the papers, patent, and patent applications cited supra deals, in large part, with the MAGE family of genes, and the unrelated BAGE and GAGE genes. It has now been found, however, that additional tumor rejection antigen precursors are expressed by cells. These tumor rejection antigen precursors are referred to as "DAGE" tumor rejection antigen precursors. They do not show homology to the MAGE family of genes, the BAGE family of genes, or the GAGE family of genes. Thus the present invention relates to genes encoding such DAGE TRAPs, the tumor rejection antigen precursors themselves as well as applications of both.

What further characterizes the DAGE tumor rejection antigen precursors is that their expression by tumor cells is much more widespread than the other tumor rejection antigen precursors described previously. This is proven infra. Yet, the expression of the family by normal cells is again limited to testis cells. Thus, a much more general means of assaying for the presence of transformed cells is available than previously. This will be seen by way of the examples.

The invention is elaborated upon further in the disclosure which follows.

BRIEF DESCRIPTION OF THE FIGURES

FIG. 1 describes, collectively, $^{51}$Cr release, cell lysis studies. In particular:

FIGS. 2A and 2B present studies on the inhibition of lysis by cytolytic T cells in the presence of an anti-HLA-A24 monoclonal antibody. Each study was carried out in the presence (FIG. 2B) or absence (FIG. 2A) of a 30 fold dilution of culture medium of a hybridoma producing the HLA-A24 specific monoclonal antibody.

FIG. 3 shows the results obtained in a TNF release assay using CTL 269/17. The stimulator cells were either LB33-MEL.B-1, COS, COS transfected with a cDNA sequence coding for HLA-A24, or COS transfected with both cDNA coding for HLA-A24, and cDNA coding for a tumor rejection antigen precursor in accordance with this invention.

DETAILED DESCRIPTION OF PREFERRED EMBODIMENTS

Example 1

Melanoma cell line LB33-MEL.B was derived from a metastasis of patient LB33, using standard techniques. Tumor cells were then cloned by limiting dilution, resulting in clone LB33-MEL.B-1, used hereafter.

Samples containing mononuclear blood cells (which include lymphocytes) were taken from patient LB33. Samples of clone LB33-MEL.B-1 were contacted to the mononuclear blood cell samples. The mixtures were observed for lysis of the LB33-MEL.B-1 cells, this lysis indicating that cytolytic T cells ("CTLs") specific for a complex of peptide and HLA molecule presented by the cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro. Prior to labelling, these cells were incubated for 48 hours, in the presence of 50 U/ml of IFN-γ to increase the expression of HLA Class I molecules. The cells were then resuspended at $10^7$ cells/ml in DMEM, supplemented with 10 mM HEPES and 30% FCS (i.e. fetal calf serum), and incubated for 45 minutes at 37° C. with 200 $\mu$Ci/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. PBL containing samples were added in 100 ul of the same medium, and assays were carried out in duplicate. Plates were centrifuged for 4 minutes at 100 g, and incubated for four hours at 37° C. in a 5.5% $CO_2$ atmosphere.

Plates were centrifuged again, 100 ul aliquots of supernatant were collected and chromium release counted. Percentage of $^{51}$Cr release was calculated as follows:

$$\% \ ^{51}\text{Cr release} = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100® to target cells.

Those mononuclear blood cell samples which showed high CTL activity were expanded and cloned via limiting dilution, and were screened again, using the same methodology.

The same method was used to test target K562 cells. When EBV-B cells were used, the only change was the replacement of DMEM medium by Hank's medium, supplemented with 5% FCS.

Figure 1C:
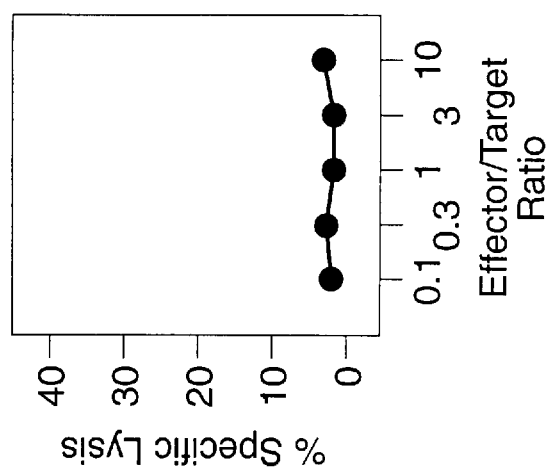
FIG. 1C shows lysis studies on NK target K562. In each of FIGS. 1A, 1B and 1C the effector cells were from CTL clone LB33-CTL-269/17.
Figure 1B:
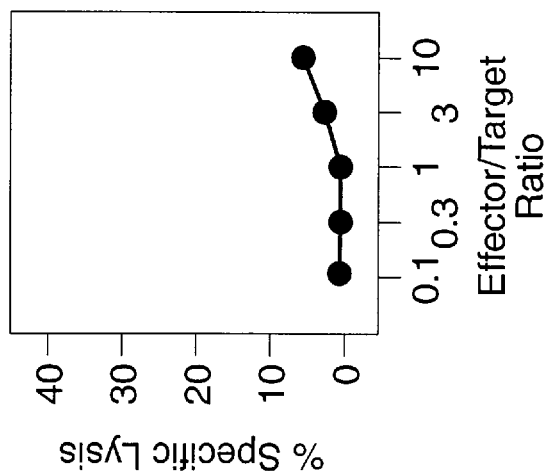
FIG. 1B shows lysis of LB33 B cells transformed by EBV. These are autologous cells.
Figure 1A:
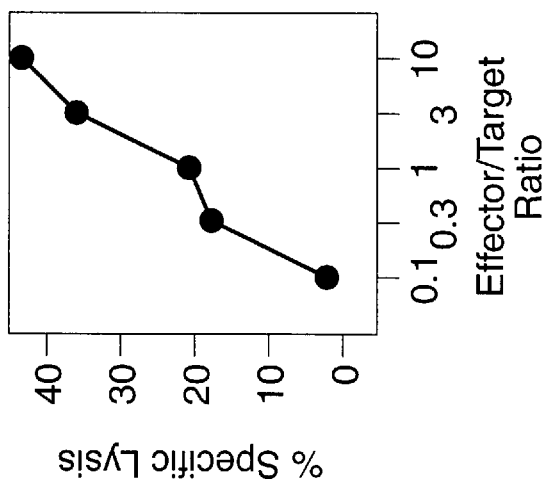
FIG. 1A shows lysis of cell line LB33-MEL.B-1.

These experiments led to isolation of CTL clone LB33-CTL-269/17 from patient LB33. As FIGS. 1A–1C indicate, this CTL clone lysed LB33-MEL.B-1 tumor cells, but not EBV transformed B cells of patient LB33, nor K562 cells. When the target cells were incubated with a monoclonal antibody specific to HLA-A24, lysis was inhibited, suggesting that any TRA peptide involved is presented by HLA-A24. FIGS. 2A and 2B show these results.

A second CTL clone, referred to as LB33-CTL-269/1, lysed LB33-MEL.B-1 but not EBV-B transformed B cells nor K562, thus suggesting that the same target antigen was recognized. Lysis by clone LB33-CTL-269/1 was also inhibited by the anti-HLA-A24 monoclonal antibody.

Example 2

Having identified the presenting MHC molecule as HLA-A24, studies were carried out to identify the coding sequence for the protein molecule, referred to hereafter as the "tumor rejection antigen precursor" or "TRAP" molecule which was the source of the presented peptide.

To do this, total RNA was isolated from cell line LB33-MEL.B-1. The mRNA was isolated using an oligo-dT binding kit, following well recognized techniques. Once the mRNA was secured, it was transcribed into cDNA, again using standard methodologies. The cDNA was then ligated to EcoRI adaptors and cloned into the EcoRI site of plasmid pcDNA-I/Amp, in accordance with manufacturer's instructions. The recombinant plasmids were then electroporated into DH5α E. coli (electroporation conditions: 1 pulse at 25 μfarads, 2500 V).

The transfected bacteria were selected with ampicillin (50 μg/ml), and then divided into 400 pools of 100 clones each. Each pool represented about 50 different cDNAs, as analysis showed that all plasmids contained an insert and cloning was not directional. Each pool was amplified to saturation, and plasmid DNA was isolated via alkaline lysis, potassium acetate precipitation and phenol extraction, following Maniatis et al., in Molecular Cloning: A Laboratory Manual (Cold Spring Harbor, N.Y., 1982). Cesium gradient centrifugation was not used.

Example 3

The amplified plasmids were then transfected into eukaryotic cells. Samples of COS-7 cells were seeded, at 15,000 cells/well into tissue culture flat bottom microwells, in Dulbecco's modified Eagles Medium ("DMEM") supplemented with 10% fetal calf serum. The cells were incubated overnight at 37° C., medium was removed and then replaced by 30 μl/well of DMEM medium containing 10% Nu serum, 400 μg/ml DEAE-dextran, 100 AM chloroquine, 100 ng of plasmid pcDNA-I/Amp-A24 and 100 ng of DNA of a pool of the cDNA library described supra. Plasmid pcDNA-I/Amp-A24 contains HLA-A24 cDNA from LB33-MEL.B, which was identified as allele HLA-A*2402. Following four hours of incubation at 37° C., the medium was removed, and replaced by 50 μl of PBS containing 10% DMSO. This medium was removed after two minutes and replaced by 200 μl of DMEM supplemented with 10% of FCS.

Following this change in medium, COS cells were incubated for 48 hours at 37° C. Medium was then discarded, and 2000 cells of described CTL clone 269/1 were added, in 100 μl of Iscove's medium containing 10% pooled human serum. Supernatant was removed after 24 hours, and TNF content was determined in an assay on WEHI cells, as described by Traversari et al., Immunogenetics 35: 145–152 (1992), the disclosure of which is incorporated by reference.

Of 400 pools tested, one was positive.

Example 4

The bacteria of the positive pool were subcloned. Plasmid DNA was extracted from 600 individual colonies, and cotransfected with pcDNA-I/Amp HLA-A24 into new samples of COS cells in the same manner as described supra, and the cells were again tested for stimulation of CTL 269/1. A positive clone was found, identified as "5E10".

The plasmid from the positive clone was removed, and sequenced following art known techniques.

The sequence contains the 1554 base pairs of SEQ ID NO: 1, and contains an open reading frame encoding 518 amino acids.

The 104 nucleotides at positions 1310–1413 were found to be identical to the first 104 base pairs of a 113 base pair sequence recorded in Genbank: L25344, HOMRBCESTC "Human (clone 17)" erythroleukemic expressed sequence tag (EST) MRNA fragment. No sequences were found which corresponded to the sequence of SEQ ID NO: 1, however.

Example 5

The information in SEQ ID NO: 1 was sufficient to permit analysis of gene expression via polymerase chain reaction (PCR).

The following primers were used:

5'-GCCTGCTGAAGGATGAGGCC-3'

5'-GGTGCTGCAGGAGACTCTGC-3'

These correspond to nucleotides 157–176, and 1328–1347 of SEQ ID NO: 1, respectively.

The PCR was carried out for 28 cycles, (1 cycle: 1 minute 94° C., 2 minutes at 65° C., 3 minutes at 72° C.). In carrying out the PCR, 2.5 ul of CDNA template, prepared as described supra, was combined with 2.5 ul of 10× Dynazyme buffer, 0.25 ul of each dNTP (10 mM), 0.5 ul of each primer (20 mM), 0.5U Dynazyme (0.25 ul stock, 2 U/ml), and 18.5 ul water. There was expression over a number of varied tumor samples. With the exception of testis, there was absolutely no expression in normal tissues.

TABLE 1

Expression of the gene corresponding to cDNA clone 5E10 in tumors and normal tissues

| Normal tissues: | |
| --- | --- |
| Liver | 0/1 |
| Stomach | 0/1 |
| Colon | 0/1 |
| Lung | 0/1 |
| Spleen | 0/1 |
| Heart | 0/1 |

TABLE 1-continued

Expression of the gene corresponding to cDNA clone 5E10 in tumors and normal tissues

| Breast | 0/1 |
| --- | --- |
| Bladder | 0/1 |
| Prostate | 0/1 |
| Thymus | 0/1 |
| Bone marrow | 0/1 |
| Blood lymphocytes | 0/1 |
| Fibroblasts | 0/1 |
| Testis | 2/2 |
| Tumor samples: | |
| Melanoma | 5/5 |
| Lymphoma | 2/5 |
| Chronic Myeloid Leukemia | 1/2 |
| Chronic Lymphoid Leukemia | 1/5 |
| Acute Myeloid Leukemia | 0/6 |
| Renal Carcinoma | 3/6 |
| Sarcoma | 2/3 |
| Breast carcinoma | 2/5 |
| Tumor cell lines: | |
| Melanoma | 11/15 |
| Leukemia | 3/6 |
| Burkitt lymphoma | 2/4 --. |

Example 6

A second assay was carried out, based upon TNF (tumor necrosis factor) release. In this assay, COS-7 cells (10,000 cells/microwell) were transfected with the plasmid pcDNAI/Amp carrying HLA-A24 cDNA, as described supra, or cotransfected with this plasmid and plasmid pcDNAI/Amp containing SEQ ID NO: 1, described supra. Twenty four hours after transfection, 3000 cells of CTL 269/17 were added to the transfectants. In a control, the same number of LB33-MEL.B-1 cells were used. The concentration of TNF released in the cell medium was measured after 24 hours, using TNF sensitive cell line WEHI-164c13.

The results are presented in FIG. 3. They show that TNF release by CTLs was provoked only with COS cells cotransfected with vectors expressing HLA-A24 and SEQ ID NO: 1. COS cells do not present HLA-A24 on their own, nor do they express the sequences of the invention. When cotransfected, however, they were able to provoke TNF release to a level nearly that of autologous cell line LB33-MEL.B-1.

The results, as set forth in FIG. 3, not only show that the material of SEQ ID NO: 1 does in fact code for a tumor rejection antigen precursor which stimulates CTLs when processed, it also shows that, as elaborated upon infra, one can assay for the presence of CTLs which are specific for tumor cells by using non-transformed cells, transfected with one or both of HLA-A24 and DAGE coding sequences, such that the resulting transfectant will express both HLA-A24 and DAGE.

The foregoing examples show the isolation of a nucleic acid molecule which codes for a tumor rejection antigen precursor. This "TRAP" coding molecule, however, is not homologous with any of the previously disclosed MAGE, BAGE or GAGE coding sequences described in the references set forth supra. Hence, one aspect of the invention is an isolated nucleic acid molecule having the nucleotide sequence set forth in SEQ ID NO: 1, as well as those portions of SEQ ID NO: 1 which express TRAs presented by MHC molecules such as HLA-A24, and derived from DAGE. This sequence is not a MAGE, BAGE or GAGE coding sequence, as will be seen by comparing it to the sequence of any of these genes as described in the cited references. Also a part of the invention are those nucleic acid molecules which code for a non-MAGE, non-BAGE and non-MAGE tumor rejection antigen precursor but which hybridize to the nucleotide sequence of SEQ ID NO: 1 under stringent conditions. The term "stringent conditions" as used herein refers to parameters with which the art is familiar. More specifically, stringent conditions, as used herein, refers to hybridization in 1M NaCl, 1% SDS, and 10% dextran sulfate. This is followed by two washes of the filter at room temperature for 5 minutes, in 2×SSC, and one wash for 30 minutes in 2×SSC, 0.1% SDS. There are other conditions, reagents, and so forth which can be used, which result in the same or higher degree of stringency. The skilled artisan will be familiar with such conditions, and, thus, they are not given here.

The widespread distribution in the expression of this gene (7 out of 8 types of tumor were found to express it), shows that the isolated nucleic acid molecule can be used as a diagnostic probe to determine presence of transformed cells. The identification of melanoma was 100%, so on a very basic level, the isolated nucleic acid molecules may be used to determine whether or not melanoma is present. Note that there are many ways available to the skilled artisan to confirm that a tumor sample is a melanoma sample, and these need not be reiterated here. Further, the rate of success in identifying tumors is in accordance with nucleic acid based diagnostic methods for determining transformation of cells.

It will also be seen from the examples that the invention embraces the use of the sequences in expression vectors, which may be used to transform or to transfect host cells and cell lines, be these prokaryotic (e.g., *E. coli*), or eukaryotic (e.g., CHO or COS cells). The expression vectors require that the pertinent sequence, i.e., one of those described supra, be operably linked to a promoter. As it has been found that human leukocyte antigen HLA-A24 presents a tumor rejection antigen derived from these genes, the expression vector may also include a nucleic acid molecule coding for HLA-A24. In a situation where the vector contains both coding sequences, it can be used to transform or transfect a cell which does not normally express either one. The tumor rejection antigen precursor coding sequence may be used alone, when, e.g., the host cell already expresses HLA-A24. Of course, there is no limit on the particular host cell which can be used. The vectors which contain the two coding sequences may be used in HLA-A24 presenting cells if desired, and the gene for tumor rejection antigen precursor can be used in host cells which do not express HLA-A24. COS cells are especially preferred.

The invention also embraces so called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

To distinguish the nucleic acid molecules and the TRAPs of the invention from the previously described MAGE, BAGE and GAGE materials, the invention shall be referred to as the DAGE family of genes and TRAPs. Hence, whenever "DAGE" is used herein, it refers to the tumor rejection antigen precursors coded for by the previously described sequences. "DAGE coding molecule" and similar terms, are used to describe the nucleic acid molecules themselves.

The invention as described herein has a number of uses, some of which are described herein. First, the invention permits the artisan to diagnose a disorder characterized by expression of the TRAP. These methods involve determining expression of the TRAP gene, and/or TRAs derived therefrom, such as a TRA presented by HLA-A24. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred. An alternate method for determination is a TNF or $^{51}$Cr release assay, of the types described supra.

The isolation of the TRAP gene also makes it possible to isolate the TRAP molecule itself, especially TRAP molecules containing the amino acid sequence coded for by SEQ ID NO: 1. These isolated molecules when presented as the TRA, or as complexes of TRA and HLA, such as HLA-A24, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to provide a CTL response, or be cells which express both molecules without transfection. Further, the TRAP molecule, its associated TRAs, as well as complexes of TRA and HLA, may be used to produce antibodies, using standard techniques well known to the art.

When "disorder" is used herein, it refers to any pathological condition where the tumor rejection antigen precursor is expressed. An example of such a disorder is cancer, melanoma in particular. Melanoma is well known as a cancer of pigment producing cells.

Therapeutic approaches based upon the disclosure are premised on a response by a subject's immune system, leading to lysis of TRA presenting cells, such as HLA-A24+ cells. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Riddel et al., Science 257: 238 (7-10-92); Lynch et al., Eur. J. Immunol. 21: 1403–1410 (1991); Kast et al., Cell 59: 603–614 (11-17-89)), cells presenting the desired complex are combined with CTLs leading to proliferation of the CTLs specific thereto. The proliferated CTLs are then administered to a subject with a cellular abnormality which is characterized by certain of the abnormal cells presenting the particular complex, where the complex contains the pertinent HLA molecule. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a DAGE sequence. Once cells presenting the relevant complex are identified via the foregoing screening methodology, they can be combined with a sample from a patient, where the sample contains CTLs. If the cells presenting the complex are lysed by the mixed CTL sample, then it can be assumed that a DAGE derived, tumor rejection antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-A24 presenting cells which then present the HLA/peptide complex of interest. The TRAP is processed to yield the peptide partner of the HLA molecule while the TRA is presented without the need for further processing.

Also a feature of this invention are isolated peptides derived from the DAGE TRAP which conform to the rules for presentation by MHC molecules. For example, in PCT application No. PCT/US93/07421, incorporated by reference herein, several motifs are described as being associated with different MHC molecules. These motifs, incorporated by reference herein, as well as those taught by, e.g. Falk et al., Nature 351: 290–296 (1991); Engelhard, Ann. Rev. Immunol 12: 181–207 (1994); Ruppert et al., Cell 74: 929–937 (1993); Rötzschke et al., Nature 348: 252–254 (1990); Bjorkman et al., Nature 329: 512–518 (1987) and Traversari et al., J. Exp. Med. 176: 1453–1457 (1992) all of which are incorporated by reference, serve as a basis for identifying appropriate peptides obtainable or derivable from the DAGE gene. These peptides may be used alone, or in mixtures, in another aspect of the invention, which is now described. Exemplary of these are the following. For HLA-A2, a binding motif is Xaa Leu Xaa Gly (Xaa)$_n$ Leu (SEQ ID NO: 2) where n is 4 or 5. Amino acids 120–128 of SEQ ID NO: 1 correspond to this motif. A second motif for HLA-A2 replaces terminal Leu with Val (SEQ ID NO: 3), and amino acids 375–384 satisfy this motif. For HLA-A3, the motifs are Xaa Leu (Xaa)$_6$ (Lys or Tyr) (SEQ ID NO: 4 and SEQ ID NO: 5). Amino acids 48–56, 100–108, 138–146, 214–222, and 257–265 of SEQ ID NO: 1 well satisfy this motif. For HLA-A11, the motif (Xaa)$_7$ Lys Lys is known, and amino acids 169–178, 214–223, and 223–232 will satisfy it. For HLA-A24, the known motif is Xaa Tyr (Xaa)$_6$ Leu, and is satisfied by amino acids 274–282, and 467–475. For HLA-B7, the motif is Xaa Pro Arg (Xaa)$_5$ Leu, and amino acids 68–76 meet it. For HLA-B8, (Xaa)$_2$ Lys Xaa Lys (Xaa)$_3$ Leu (SEQ ID NO: 9) is the motif, satisfied by amino acids 176–184 and 218–226. For HLA-B44, motif Xaa Glu (Xaa)$_3$ Asp (Xaa)$_2$ Phe (SEQ ID NO: 10) is satisfied by amino acids 204–212. For HLA-Cw* 1601, the motif Xaa Ala (Xaa)$_6$ Leu (SEQ ID NO: 11) is satisfied by amino acids 60–68, and 395–403.

The fact that a number of sequences are present which correspond to HLA motifs suggests what will be referred to herein as "cocktail" therapeutic and diagnostic uses. It is expected that in a typical CTL response to tumor cells, CTLs specific to more than one complex of peptide and HLA molecule will proliferate. For example, it may be the case that for HLA-A24 presenting cells, CTLs specific for HLA-A24 plus amino acid sequence 274–282, and CTLs specific for HLA-A24 and amino acid sequence 467–475 will proliferate. Thus, one can optimize the assay by using both peptides when attempting to identify CTLs. Similarly, the therapeutic methods might be optimized by using more than one HLA-A24 binding peptide.

It is well known that individuals are not "monovalent" for HLA molecules, as cells present more than one kind of HLA. Thus, one can maximize diagnostic and/or therapeutic by combining a number of peptides as described supra in a diagnostic assay to determine CTLs, or to treat patients in the therapies described supra.

Any concern as to false positives, is believed to be misplaced because, as noted supra, the nucleic acid molecules of the invention have been found to be expressed only in tumor cells, so the presence of CTLs to the HLA and the peptides must be considered de facto evidence of the presence, at some time in the past of the present existence of a cancerous or transformed condition. Thus, cocktails of the peptides of the invention can be prepared. Determination of the components of the mixture is not difficult, because all that is needed is one or more of the HLA types presented by the individual under consideration. HLA typing is a very standard technique, well known in the art; and well within the abilities and skill of the artisan.

It has been fairly well established that the blood of individuals afflicted with tumors frequently contains cytolytic T cells ("CTLs") against complexes of MHC molecules and presented peptides. See, e.g., Robbins et al., Canc. Res. 54: 3124–3126 (1994); Topolian et al., J. Immunol. 142: 3714–3725 (1989); Coulie et al., Int. J. Cancer 50: 289–297 (1992), all of which are incorporated by reference. Also, note Kawakami et al., J. Exp. Med. 180: 347–352 (1994); Hom et al., J. Immunother 10: 153–164 (1991), Darrow et al, J. Immunol. 142 (9): 3329–3335 (1989); Slovin et al., J. Immunol. 137(9): 3042–3048 (1986), all of which are incorporated by reference. These papers all establish the usefulness of a CTL proliferation assay to diagnose cancer. Expressed generally, one takes a peripheral blood lymphocyte (PBL) containing sample from a subject to be tested. Assuming that the patient does have a tumor, or the subject's cells have began to undergo transformation, CTLs which are specific to transformed cells with be contained in that sample. These CTLs can be stimulated to proliferate via contact with a target cell which presents complexes of a relevant MHC molecule and the peptide presented thereby. For example, as was shown, supra, DAGE derived tumor rejection antigens ("TRAs") are presented by HLA-A24 cells. Thus, by mixing the PBL containing sample with a target of HLA-A24 presenting cells and peptides which are derived from a TRAP and presented by HLA-A24, one can observe CTL proliferation, and thus diagnose for the presence of transformed cells. These cells can be cells which normally present the MHC molecule in question, but can also be cells transformed by an HLA coding sequence. The cells may be tumor cells, or normal cells. Various ways of determining CTL proliferation are known, including TNF release assays, and $^{51}$Cr release assays. Other methodologies are also available. Thus, one aspect of the invention involves mixing a target cell sample with a peptide or mix of peptides derived from a DAGE TRAP and presented by the MHC molecules of the target cell sample and with the PBLs of the subject under evaluation. The mixture is then tested for CTL proliferation.

The peptide or peptides may also be combined with one or more adjuvants which stimulate a more pronounced CTL response. Exemplary of such adjuvants are saponins and their derivatives, such as those disclosed by U.S. Pat. No. 5,057,540 to Kensil et al., incorporated by reference or PCT application PCT/US92/03579 to Scott et al., also incorporated by reference. Of course, standard adjuvants, such as Freund's complete adjuvant, or Freund's incomplete adjuvant, may also be used. Other materials associated with enhancing T cell proliferation, such as cytokines, especially interleukins, such as IL-12, may also be added.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule that encodes for a DAGE tumour rejection antigen precursor as defined by the nucleotide sequence set forth in SEQ. ID. NO: 1.

2. An isolated nucleic acid molecule which hybridizes, under stringent conditions, to the nucleic acid molecule set forth in SEQ ID No: 1, and codes for a tumor rejection antigen precursor, with the proviso that said isolated nucleic acid molecule does not code for any of: a MAGE tumor rejection antigen precursor, a BAGE tumor rejection antigen precursor, a GAGE tumor rejection antigen precursor.

3. An isolated MRNA molecule which is complementary to the nucleic acid molecule of claim 1, and codes for a tumor rejection antigen precursor of SEQ ID No: 1.

4. A host cell transfected or transformed with the nucleic acid molecule of claim 1.

5. A host cell transfected or transformed with the nucleic acid molecule of claim 2.

6. An expression vector comprising the isolated nucleic acid molecule of claim 1 operably linked to a promoter.

7. An expression vector comprising the isolated nucleic acid molecule of claim 2 operably linked to a promoter.

8. The host cell of claim 4, wherein said host cell is a mammalian cell which expresses HLA-A24.

9. The host cell of claim 5, wherein said host cell is a mammalian cell which expresses HLA-A24.

10. The expression vector of claim 6, further comprising a nucleic acid molecule which codes for HLA-A24.

11. The expression vector of claim 7, further comprising a nucleic acid molecule which codes for HLA-A24.

12. Expression kit comprising a separate portion of each of:

(i) the isolated nucleic acid molecule of claim 1, and (ii) a nucleic acid molecule which codes for HLA-A24.

13. Expression kit comprising a separate portion of each of:

(i) the isolated nucleic acid molecule of claim 2, and;

(ii) a nucleic acid molecule which codes for HLA-A24.

14. An isolated tumor rejection antigen precursor coded by the nucleic acid molecule of claim 1, or 2.

* * * * *

UNITED STATES PATENT AND TRADEMARK OFFICE
CERTIFICATE OF CORRECTION

PATENT NO. : 5,830,753
DATED : Nov. 3, 1998
INVENTOR(S) : Coulie et al.

It is certified that error appears in the above-identified patent and that said Letters Patent is hereby corrected as shown below:

On the cover, in the section titled References Cited, Other Publications, second column, line 11, change "Antigrn" to -- Antigen --.

In column 4, last line, change "AM" to -- $\mu$M --.
In column 5, line 34, change "MRNA" to -- mRNA --.
In column 5, line 48, change "CDNA" to -- cDNA --.

Signed and Sealed this

Thirty-first Day of October, 2000

Attest:

Q. TODD DICKINSON

Attesting Officer          Director of Patents and Trademarks

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
        ( A ) LENGTH: 1555 base pairs
        ( B ) TYPE: nucleic acid
        ( C ) STRANDEDNESS:single
        ( D ) TOPOLOGY: linear ( i i ) MOLECULE TYPE: nucleic acid ( i x ) FEATURE:
        ( A ) NAME/KEY: DAGE
        ( D ) OTHER INFORMATION: Xaa is Arg when V is C or A or
            Gly when V is G ( x i ) SEQUENCE DESCRIPTION: SEQ ID NO: 1:

| VGA | CTG | AGA | CCT | AGA | AAT | CCA | AGC | GTT | GGA | GGT | CCT | GAG | GCC | AGC | CTA | 48 |
|---|---|---|---|---|---|---|---|---|---|---|---|---|---|---|---|---|
| Xaa | Leu | Arg | Pro | Arg | Asn | Pro | Ser | Val | Gly | Gly | Pro | Glu | Ala | Ser | Leu | |
| 1 | | | | 5 | | | | | 10 | | | | | 15 | | |
| AGT | CGC | TTC | AAA | ATG | GAA | CGA | AGG | CGT | TTG | CGG | GGT | TCC | ATT | CAG | AGC | 96 |
| Ser | Arg | Phe | Lys | Met | Glu | Arg | Arg | Arg | Leu | Arg | Gly | Ser | Ile | Gln | Ser | |
| | | | 20 | | | | | 25 | | | | | 30 | | | |
| CGA | TAC | ATC | AGC | ATG | AGT | GTG | TGG | ACA | AGC | CCA | CGG | AGA | CTT | GTG | GAG | 144 |
| Arg | Tyr | Ile | Ser | Met | Ser | Val | Trp | Thr | Ser | Pro | Arg | Arg | Leu | Val | Glu | |
| | | 35 | | | | | 40 | | | | | 45 | | | | |
| CTG | GCA | GGG | CAG | AGC | CTG | CTG | AAG | GAT | GAG | GCC | CTG | GCC | ATT | GCC | GCC | 192 |
| Leu | Ala | Gly | Gln | Ser | Leu | Leu | Lys | Asp | Glu | Ala | Leu | Ala | Ile | Ala | Ala | |
| | 50 | | | | | 55 | | | | | 60 | | | | | |
| CTG | GAG | TTG | CTG | CCC | AGG | GAG | CTC | TTC | CCG | CCA | CTC | TTC | ATG | GCA | GCC | 240 |
| Leu | Glu | Leu | Leu | Pro | Arg | Glu | Leu | Phe | Pro | Pro | Leu | Phe | Met | Ala | Ala | |
| 65 | | | | | 70 | | | | | 75 | | | | | 80 | |
| TTT | GAC | GGG | AGA | CAC | AGC | CAG | ACC | CTG | AAG | GCA | ATG | GTG | CAG | GCC | TGG | 288 |
| Phe | Asp | Gly | Arg | His | Ser | Gln | Thr | Leu | Lys | Ala | Met | Val | Gln | Ala | Trp | |
| | | | | 85 | | | | | 90 | | | | | 95 | | |
| CCC | TTC | ACC | TGC | CTC | CCT | CTG | GGA | GTG | CTG | ATG | AAG | GGA | CAA | CAT | CTT | 336 |
| Pro | Phe | Thr | Cys | Leu | Pro | Leu | Gly | Val | Leu | Met | Lys | Gly | Gln | His | Leu | |
| | | | 100 | | | | | 105 | | | | | 110 | | | |
| CAC | CTG | GAG | ACC | TTC | AAA | GCT | GTG | CTT | GAT | GGA | CTT | GAT | GTG | CTC | CTT | 384 |
| His | Leu | Glu | Thr | Phe | Lys | Ala | Val | Leu | Asp | Gly | Leu | Asp | Val | Leu | Leu | |
| | | 115 | | | | | 120 | | | | | 125 | | | | |
| GCC | CAG | GAG | GTT | CGC | CCC | AGG | AGG | TGG | AAA | CTT | CAA | GTG | CTG | GAT | TTA | 432 |
| Ala | Gln | Glu | Val | Arg | Pro | Arg | Arg | Trp | Lys | Leu | Gln | Val | Leu | Asp | Leu | |
| | 130 | | | | | 135 | | | | | 140 | | | | | |
| CGG | AAG | AAC | TCT | CAT | CAG | GAC | TTC | TGG | ACT | GTA | TGG | TCT | GGA | AAC | AGG | 480 |

```
Arg Lys Asn Ser His Gln Asp Phe Trp Thr Val Trp Ser Gly Asn Arg
145                 150                 155                 160

GCC AGT CTG TAC TCA TTT CCA GAG CCA GAA GCA GCT CAG CCC ATG ACA       528
Ala Ser Leu Tyr Ser Phe Pro Glu Pro Glu Ala Ala Gln Pro Met Thr
                165                 170                 175

AAG AAG CGA AAA GTA GAT GGT TTG AGC ACA GAG GCA GAG CAG CCC TTC       576
Lys Lys Arg Lys Val Asp Gly Leu Ser Thr Glu Ala Glu Gln Pro Phe
            180                 185                 190

ATT CCA GTA GAG GTG CTC GTA GAC CTG TTC CTC AAG GAA GGT GCC TGT       624
Ile Pro Val Glu Val Leu Val Asp Leu Phe Leu Lys Glu Gly Ala Cys
        195                 200                 205

GAT GAA TTG TTC TCC TAC CTC ATT GAG AAA GTG AAG CGA AAG AAA AAT       672
Asp Glu Leu Phe Ser Tyr Leu Ile Glu Lys Val Lys Arg Lys Lys Asn
    210                 215                 220

GTA CTA CGC CTG TGC TGT AAG AAG CTG AAG ATT TTT GCA ATG CCC ATG       720
Val Leu Arg Leu Cys Cys Lys Lys Leu Lys Ile Phe Ala Met Pro Met
225                 230                 235                 240

CAG GAT ATC AAG ATG ATC CTG AAA ATG GTG CAG CTG GAC TCT ATT GAA       768
Gln Asp Ile Lys Met Ile Leu Lys Met Val Gln Leu Asp Ser Ile Glu
                245                 250                 255

GAT TTG GAA GTG ACT TGT ACC TGG AAG CTA CCC ACC TTG GCG AAA TTT       816
Asp Leu Glu Val Thr Cys Thr Trp Lys Leu Pro Thr Leu Ala Lys Phe
                260                 265                 270

TCT CCT TAC CTG GGC CAG ATG ATT AAT CTG CGT AGA CTC CTC CTC TCC       864
Ser Pro Tyr Leu Gly Gln Met Ile Asn Leu Arg Arg Leu Leu Leu Ser
            275                 280                 285

CAC ATC CAT GCA TCT TCC TAC ATT TCC CCG GAG AAG GAA GAG CAG TAT       912
His Ile His Ala Ser Ser Tyr Ile Ser Pro Glu Lys Glu Glu Gln Tyr
        290                 295                 300

ATC GCC CAG TTC ACC TCT CAG TTC CTC AGT CTG CAG TGC CTG CAG GCT       960
Ile Ala Gln Phe Thr Ser Gln Phe Leu Ser Leu Gln Cys Leu Gln Ala
305                 310                 315                 320

CTC TAT GTG GAC TCT TTA TTT TTC CTT AGA GGC CGC CTG GAT CAG TTG      1008
Leu Tyr Val Asp Ser Leu Phe Phe Leu Arg Gly Arg Leu Asp Gln Leu
                325                 330                 335

CTC AGG CAC GTG ATG AAC CCC TTG GAA ACC CTC TCA ATA ACT AAC TGC      1056
Leu Arg His Val Met Asn Pro Leu Glu Thr Leu Ser Ile Thr Asn Cys
                340                 345                 350

CGG CTT TCG GAA GGG GAT GTG ATG CAT CTG TCC AGA GTC CCA GCG TC       1104
Arg Leu Ser Glu Gly Asp Val Met His Leu Ser Gln Ser Pro Ser Val
            355                 360                 365

AGT CAG CTA AGT GTC CTG AGT CTA AGT GGG GTC ATG CTG ACC GAT GTA      1152
Ser Gln Leu Ser Val Leu Ser Leu Ser Gly Val Met Leu Thr Asp Val
        370                 375                 380

AGT CCC GAG CCC CTC CAA GCT CTG CTG GAG AGA GCC TCT GCC ACC CTC      1200
Ser Pro Glu Pro Leu Gln Ala Leu Leu Glu Arg Ala Ser Ala Thr Leu
385                 390                 395                 400

CAG GAC CTG GTC TTT GAT GAG TGT GGG ATC ACG GAT GAT CAG CTC CTT      1248
Gln Asp Leu Val Phe Asp Glu Cys Gly Ile Thr Asp Asp Gln Leu Leu
                405                 410                 415

GCC CTC CTG CCT TCC CTG AGC CAC TGC TCC CAG CTT ACA ACC TTA AGC      1296
Ala Leu Leu Pro Ser Leu Ser His Cys Ser Gln Leu Thr Thr Leu Ser
                420                 425                 430

TTC TAC GGG AAT TCC ATC TCC ATA TCT GCC TTG CAG AGT CTC CTG CAG      1344
Phe Tyr Gly Asn Ser Ile Ser Ile Ser Ala Leu Gln Ser Leu Leu Gln
            435                 440                 445

CAC CTC ATC GGG CTG AGC AAT CTG ACC CAC GTG CTG TAT CCT GTC CCC      1392
His Leu Ile Gly Leu Ser Asn Leu Thr His Val Leu Tyr Pro Val Pro
        450                 455                 460

CTG GAG AGT TAT GAG GAC ATC CAT GGT ACC CTC CAC CTG GAG AGG CTT      1440
```

| Leu | Glu | Ser | Tyr | Glu | Asp | Ile | His | Gly | Thr | Leu | His | Leu | Glu | Arg | Leu | |
|-----|-----|-----|-----|-----|-----|-----|-----|-----|-----|-----|-----|-----|-----|-----|-----|---|
| 465 |     |     |     |     | 470 |     |     |     | 475 |     |     |     |     |     | 480 |   |

| GCC | TAT | CTG | CAT | GCC | AGG | CTC | AGG | GAG | TTG | CTG | TGT | GAG | TTG | GGG | CGG | 1488 |
| Ala | Tyr | Leu | His | Ala | Arg | Leu | Arg | Glu | Leu | Leu | Cys | Glu | Leu | Gly | Arg |      |
|     |     |     |     | 485 |     |     |     | 490 |     |     |     |     |     | 495 |     |      |

| CCC | AGC | ATG | GTC | TGG | CTT | AGT | GCC | AAC | CCC | TGT | CCT | CAC | TGT | GGG | GAC | 1536 |
| Pro | Ser | Met | Val | Trp | Leu | Ser | Ala | Asn | Pro | Cys | Pro | His | Cys | Gly | Asp |      |
|     |     |     | 500 |     |     |     |     | 505 |     |     |     |     | 510 |     |     |      |

| AGA | ACC | TTC | TAT | GAC | CCG | G | 1555 |
| Arg | Thr | Phe | Tyr | Asp | Pro |   |      |
|     |     |     | 515 |     |     |   |      |

( 2 ) INFORMATION FOR SEQ ID NO: 2:

( i ) SEQUENCE CHARACTERISTICS:
        ( A ) LENGTH: 10 amino acids
        ( B ) TYPE: amino acid
        ( D ) TOPOLOGY: linear ( i x ) FEATURE:
        ( D ) OTHER INFORMATION: The last Xaa may be present or absent. Each Xaa is any amino acid.

( x i ) SEQUENCE DESCRIPTION: SEQ ID NO: 2:

| Xaa | Leu | Xaa | Gly | Xaa | Xaa | Xaa | Xaa | Xaa | Leu |
|-----|-----|-----|-----|-----|-----|-----|-----|-----|-----|
|     |     |     |     | 5   |     |     |     |     | 10  |

( 2 ) INFORMATION FOR SEQ ID NO: 3:

( i ) SEQUENCE CHARACTERISTICS:
        ( A ) LENGTH: 10 amino acids
        ( B ) TYPE: amino acid
        ( D ) TOPOLOGY: linear ( i x ) FEATURE:
        ( D ) OTHER INFORMATION: The last Xaa may be present or absent. Each Xaa is any amino acid.

( x i ) SEQUENCE DESCRIPTION: SEQ ID NO: 3:

| Xaa | Leu | Xaa | Gly | Xaa | Xaa | Xaa | Xaa | Xaa | Val |
|-----|-----|-----|-----|-----|-----|-----|-----|-----|-----|
|     |     |     |     | 5   |     |     |     |     | 10  |

( 2 ) INFORMATION FOR SEQ ID NO: 4:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( D ) OTHER INFORMATION: Each Xaa may be any amino acid.

( x i ) SEQUENCE DESCRIPTION: SEQ ID NO: 4:

| Xaa | Leu | Xaa | Xaa | Xaa | Xaa | Xaa | Xaa | Lys |
|-----|-----|-----|-----|-----|-----|-----|-----|-----|
|     |     |     |     | 5   |     |     |     |     |

( 2 ) INFORMATION FOR SEQ ID NO: 5:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( D ) OTHER INFORMATION: Each Xaa may be any amino acid.

( x i ) SEQUENCE DESCRIPTION: SEQ ID NO: 5:

| Xaa | Leu | Xaa | Xaa | Xaa | Xaa | Xaa | Xaa | Tyr |
|-----|-----|-----|-----|-----|-----|-----|-----|-----|
|     |     |     |     | 5   |     |     |     |     |

( 2 ) INFORMATION FOR SEQ ID NO: 6:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( D ) OTHER INFORMATION: Each Xaa may be any amino acid.

( x i ) SEQUENCE DESCRIPTION: SEQ ID NO: 6:

Xaa Xaa Xaa Xaa Xaa Xaa Xaa Lys Lys
               5

( 2 ) INFORMATION FOR SEQ ID NO: 7:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( D ) OTHER INFORMATION: Each Xaa may be any amino acid.

( x i ) SEQUENCE DESCRIPTION: SEQ ID NO: 7:

Xaa Tyr Xaa Xaa Xaa Xaa Xaa Xaa Leu
               5

( 2 ) INFORMATION FOR SEQ ID NO: 8:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( D ) OTHER INFORMATION: Each Xaa may be any amino acid.

( x i ) SEQUENCE DESCRIPTION: SEQ ID NO: 8:

Xaa Pro Arg Xaa Xaa Xaa Xaa Xaa Leu
               5

( 2 ) INFORMATION FOR SEQ ID NO: 9:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( D ) OTHER INFORMATION: Each Xaa may be any amino acid.

( x i ) SEQUENCE DESCRIPTION: SEQ ID NO: 9:

Xaa Xaa Lys Xaa Lys Xaa Xaa Xaa Leu
               5

( 2 ) INFORMATION FOR SEQ ID NO: 10:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( D ) OTHER INFORMATION: Each Xaa may be any amino acid.

( x i ) SEQUENCE DESCRIPTION: SEQ ID NO: 10:

Xaa Glu Xaa Xaa Xaa Asp Xaa Xaa Phe
               5

( 2 ) INFORMATION FOR SEQ ID NO: 11:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( D ) OTHER INFORMATION: Each Xaa may be any amino acid.

( x i ) SEQUENCE DESCRIPTION: SEQ ID NO: 11:

Xaa Ala Xaa Xaa Xaa Xaa Xaa Xaa Leu
                5